United States Patent [19]

Campbell

[11] Plant 4,896

[45] Oct. 19, 1982

[54] ALMOND TREE (RENE)

[75] Inventor: Rene M. Campbell, 3372 S. Burchell Ave., Le Grand, Calif. 95333

[73] Assignee: Rene M. Campbell, Le Grand, Calif.

[21] Appl. No.: 239,342

[22] Filed: Mar. 2, 1981

[51] Int. Cl.[3] ..... A01H 5/00

[52] U.S. Cl. ..... Plt./30

[58] Field of Search ..... Plt./30

*Primary Examiner*—James R. Feyrer

*Attorney, Agent, or Firm*—Roger B. Webster

[57] ABSTRACT

A self-sterile almond tree which is rapid and vigorous in growth, medium size, spreading, and early producing; foliated in medium quantity with medium size, lanceolate, acutely pointed leaves having a crenate margin and alternate, medium size, globose, green glands; blooms late with pink flowers; and is a regular and very heavy producer, with a medium harvest period, of large, clustered nuts having large, elongated, plump kernels.

1 Drawing Figure

BACKGROUND OF THE VARIETY

1. Field of the Invention

As an orchardist, in the field of almond culture, I am interested in the creation of new varieties, and to this end I have — over a substantial span of time — conducted an experimental almond orchard, and in which the present variety of almond tree was originated by me; such experimental orchard being located on my ranch near Le Grand, Merced County, Calif.

2. Classification of the Variety

The present new and distinct variety of almond tree is embraced by subclass 30, Plants, of the U.S. Patent Office Manuel of Classification 3. Prior Varieties Among the existent varieties of almond trees which are known to me, and mentioned herein, are Carmel (U.S. Plant Pat. No. 2,641), Mission (unpatented), and Ne Plus Ultra (unpatented).

ORIGIN OF THE VARIETY

The present variety of almond tree was originated by me as follows:

A number of seedlings — produced from seed gathered from an unnamed almond tree growing in a corner of my ranch, located as aforesaid — were grown in my experimental orchard on such ranch; such seedlings having been maintained under careful and continuing observation by me. In maturity, one of such seedlings — which is the present variety — evidenced certain novel characteristics and was, therefore, selected for asexual reproduction and possible commercialization.

ASEXUAL REPRODUCTION OF THE VARIETY

The present variety of almond tree was asexually reproduced, by me on my said ranch, by grafting on a number of rootstocks, and — in maturity — such reproductions ran true to the original seedling-grown tree in all respects.

SUMMARY OF THE VARIETY

The present variety of self-sterile almond tree is, characteristically, rapid and vigorous in growth, medium size, spreading, and early producing; foliated in medium quantity with medium size, lanceolate, acutely-pointed leaves having a crenate margin and alternate, medium size, globose, green glands; blooms late with pink flowers; and is a regular and very heavy producer, with a medium harvest period, of large, clustered nuts having large, elongated, plump kernels.

The present variety of almond tree is further characterized, in comparison to the Carmel, by a more hardy, medium-size tree, whereas the Carmel tree is of small size; by interfertility but blooming with pink rather than white flowers and approximately two days later; and by nuts which are better sealed and hence more insect-resistant.

The present variety of almond tree is still further characterized by a blooming period approximately one day before Mission.

The present variety of almond tree is still further characterized by a high percentage of nut set in relation to the quantity of bloom.

The present variety of almond tree is still further characterized by a harvest period which is substantially concurrent with the Ne Plus Ultra.

BRIEF DESCRIPTION OF THE DRAWING

The drawing is an illustration, by photographic reproduction in color, of — in one view — a twig with leaves, and, separately, in another view, nuts in hull, nuts out of hull, and kernels out of shell.

DESCRIPTION OF THE VARIETY

The botanical details of this new and distinct variety of almond tree — with color definitions in common color terms — are as follows:

Tree:

*Density.*—Open.

*Size.*—Medium.

*Vigor.*—Vigorous.

*Hardiness.*—More hardy than Carmel.

Trunk:

*Form.*—Stocky.

*Texture.*—Medium.

Branches:

*Form.*—Medium.

*Texture.*—Smooth.

*Lenticels.*—Numerous. Large.

*Branching habit.*—Spreading.

*Color.*—New wood: red — green. Glossy. Mature wood: brown — green. Glossy.

Foliage:

*Quantity.*—Medium.

Leaves:

*Size.*—Medium. Average length — 4-13/16". Average width — 1¼".
*Shape.*—Lanceolate. Abruptly pointed.
*Thickness.*—Medium.
*Texture.*—Smooth.
*Margin.*—Crenate.
*Petiole.*—Long. Medium thickness.
*Glands.*—Average number — 4. Alternate. Medium size. Globose. Green. Positioned on petiole and base of blade.
*Stipules.*—None.
*Color.*—Top side — dark green. Under side — slightly lighter green.

Bloom:
*Amount of bloom.*—Average. Clustered.
*Color.*—Pink.
*Blooming period.*—Late — Feb. 28 - Mar. 1, 1980. One day before Mission, and two days after Carmel.
*Fertility.*—Self-sterile. Interfertile with Carmel.

Crop:
*Bearing.*—Regular bearer.
*Productivity.*—Very heavy. High percentage of fruit set in ratio to bloom. Produces well in wet seasons.
*Distribution of nuts on tree.*—In clusters on short spurs.
*Harvest period.*—Medium — Sept. 18, 1980. With Ne Plus Ultra.
*Tenacity.*—Hangs well on tree. Easy to harvest. Easy to hull.

Hull:
*Outer surface.*—Smooth.
*Pits.*—Absent.
*Form.*—Regular.
*Thickness.*—Thin.
*Flesh.*—Tough.
*Suture.*—Flat depressed.
*Color.*—Light green without a silvery sheen.
*Dehiscence.*—Opens freely.
*Splitting.*—Along suture.

Nut:
*Size.*—Large. Average length — 1-5/16". Average width — 13/16". Average thickness — ⅝". Average weight — 10 nuts per ounce.
*Form.*—Length/width: elongated. Width/thickness: plump.

*Shell.*—Hard. Thin. Outer shell: crumbling. Inner shell: hard. Well sealed.
*Color.*—Medium light brown.
*Pits.*—Small. Numerous. Deep. Irregular.
*Base.*—Dorsally oblique.
*Stem scar.*—Large. Obtuse.
*Apex.*—Acute.
*Wing.*—Narrow. Thin. Tapered toward base.
*Inner surface.*—Dark colored.
*Ventral streak.*—Dark. Narrow. Long. Point acute.
*Percentage of kernel to nut.*—Range — 49%-56%.

Kernel:
*Size.*—Large. Average length — ⅞". Average width — ½". Average thickness — 5/16". Average weight — 22 kernels per ounce.
*Form.*—Length/width: elongated. Width/thickness: plump.
*Base.*—Dorsally oblique.
*Stem scar.*—Large. Obtuse.
*Apex.*—Acute. Sharp. Shouldered. Prolonged at tip.
*Texture.*—Furrowed.
*Pellicle.*—Thick.
*Pubescence.*—Smooth.
*Color.*—Medium light brown.
*Number of doubles.*—Few.
*Flavor.*—Normal.
*Quality.*—Good.

Susceptibility or resistance to insects and diseases: Resistant to brown rot and naval orange worm.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, characterized, in comparison to the Carmel, by a more hardy, medium-size tree, whereas the Carmel tree is of small size; by interfertility but blooming with pink rather than white flowers and approximately two days later; and by nuts which are better sealed and hence more insect resistant; and further characterized by a blooming period approximately one day before Mission; by a high percentage of nut set in relation to the quantity of bloom; and by a harvest period substantially concurrent with the Ne Plus Ultra.

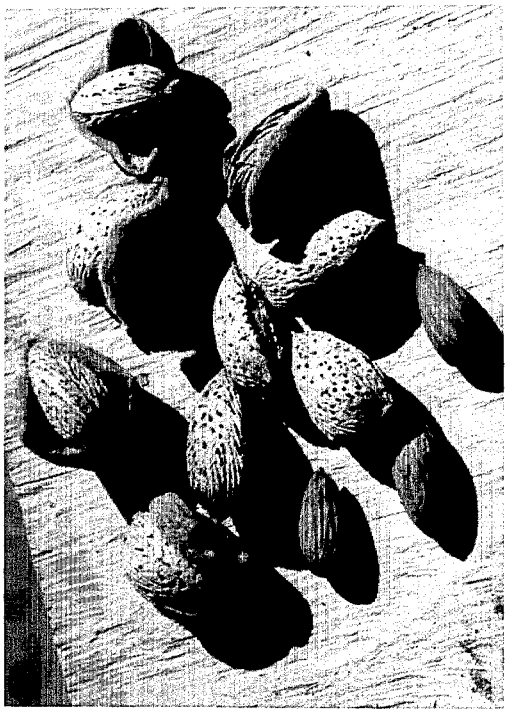
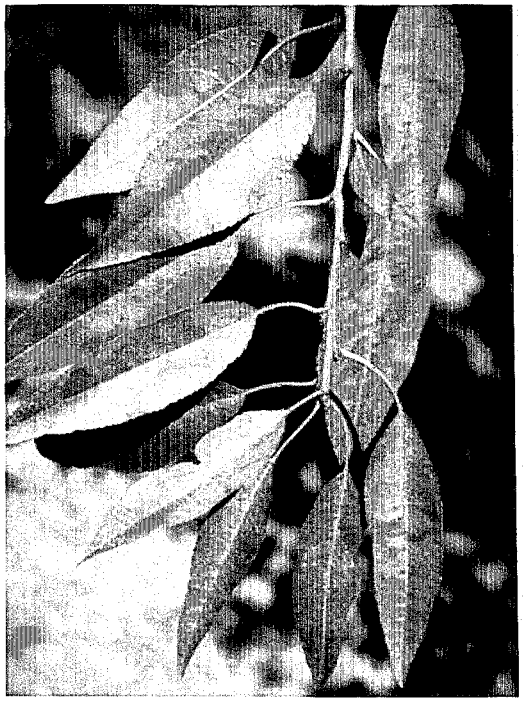

* * * * *